United States Patent
Winter et al.

(10) Patent No.: US 8,389,562 B2
(45) Date of Patent: Mar. 5, 2013

(54) POLYMORPHIC FORMS OF A 3-PYRROLE SUBSTITUTED 2-INDOLINONE

(75) Inventors: Stephen Benedict David Winter, Santa Coloma de Cervelló (ES); Bernardino Mangion, Santa Lucia (MT)

(73) Assignee: Medichem, S.A. (ES)

( * ) Notice: Subject to any disclaimer, the term of this patent is extended or adjusted under 35 U.S.C. 154(b) by 148 days.

(21) Appl. No.: 12/747,762

(22) PCT Filed: Dec. 12, 2008

(86) PCT No.: PCT/IB2008/003458
§ 371 (c)(1),
(2), (4) Date: Jul. 13, 2010

(87) PCT Pub. No.: WO2009/074862
PCT Pub. Date: Jun. 18, 2009

(65) Prior Publication Data
US 2010/0286410 A1    Nov. 11, 2010

Related U.S. Application Data

(60) Provisional application No. 61/013,117, filed on Dec. 12, 2007.

(51) Int. Cl.
*A61K 31/404*    (2006.01)
*C07D 403/06*    (2006.01)

(52) U.S. Cl. .................................... 514/414; 548/468
(58) Field of Classification Search ............... 514/414; 548/468
See application file for complete search history.

(56) References Cited

U.S. PATENT DOCUMENTS

2002/0156292 A1    10/2002    Tang et al.
2003/0069298 A1*   4/2003     Hawley et al. ............... 514/414
2010/0256392 A1*   10/2010    Gavenda et al. ............. 548/468

OTHER PUBLICATIONS

IUPAC Gold Book, Definition of "chemical reaction", obtained from http://goldbook.iupac.org/C01033.html on Apr. 11, 2012.*

* cited by examiner

*Primary Examiner* — Joseph Kosack
*Assistant Examiner* — Matthew Coughlin
(74) *Attorney, Agent, or Firm* — Leydig, Voit & Mayer, Ltd.

(57) ABSTRACT

The invention relates to new crystalline polymorphic forms of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (i.e., sunitinib base), including Form I, Form II, and Form IV, processes for preparing crystalline polymorphic forms of sunitinib base, and pharmaceutically acceptable salts of new crystalline polymorphic forms of sunitinib base and pharmaceutical compositions comprising new crystalline polymorphic forms of sunitinib base, salts of new crystalline polymorphic forms of sunitinib base and mixtures thereof.

3 Claims, 15 Drawing Sheets

POLYMORPHIC FORMS OF A 3-PYRROLE SUBSTITUTED 2-INDOLINONE

CROSS-REFERENCE TO RELATED APPLICATIONS

This patent application claims the benefit of U.S. Provisional Patent Application No. 61/013,117, filed Dec. 12, 2007, which is incorporated by reference.

BACKGROUND OF THE INVENTION

Sunitinib (Compound I) is the international commonly accepted name for N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide, and has an empirical formula of $C_{22}H_{27}FN_4O_2$, and a molecular weight of 398.47. Sunitinib is an active pharmaceutical substance indicated for the treatment of abnormal cell growth, such as cancer, in mammals, particularly in humans.

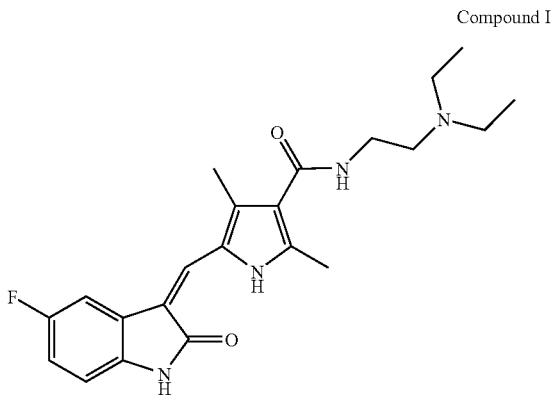 [SMILES: CCN(CC)CCNC(=O)c1c(C)[nH]c(/C=C2\C(=O)Nc3ccc(F)cc32)c1C]

Compound I

The malate salt of sunitinib has been selected for medical purpose and is commercially marketed under the trade name of SUTENT™ for the treatment of renal cell carcinoma and gastrointestinal stromal tumors.

Sunitinib base and its malate salt are described in U.S. Pat. No. 6,573,293 ("the '293 patent"), which is incorporated herein by reference. In particular, Example 80 (Alternative Synthesis) of the '293 patent describes the preparation of sunitinib base via condensation of 5-fluoro-1,3-dihydroindol-2-one and N-[2-(diethylamino)ethyl]-5-formyl-2,4-dimethyl-1H-pyrrole-3-carboxamide, in the presence of pyrrolidine and ethanol.

Applicants have prepared sunitinb base following the teachings of Example 80 (Alternative Synthesis) of the '293 patent (i.e., see Comparative Example 1 of the present invention) and the crystalline form of sunitinib base obtained, referred to herein as sunitinib base Form III, has been characterized herein by X-ray powder diffraction (XRD), infrared (IR) spectroscopy, and differential scanning calorimetry (DSC).

Applicants have observed that the sunitinib base obtained in the prior art (i.e., sunitinib base Form III) presents a low solubility profile, which makes dissolving sunitinib and the preparation of corresponding pharmaceutically acceptable salts troublesome. This observation is in accordance with the European Public Assessment Report provided for SUTENT™ which discloses that sunitinib is classified as a low solubility compound according to the biopharmaceutical classification. In this regard, the low solubility of sunitinib base Form III would involve the use of large amounts of suitable solvents or mixture of solvents and/or the use of particular conditions aimed to improve the solubility of sunitinib base Form III and/or long reaction times for processes using sunitinib, which may represent an important drawback, especially for processes on an industrial scale.

Furthermore, no other polymorph of sunitinib, other than sunitinib base Form III, is reported in the literature. Additionally, there is no crystal structure data in the literature for sunitinib base Form III.

Polymorphism is common among chemical substances and is commonly defined as the ability of a substance to exist in two or more crystalline phases that have a different arrangement and/or conformation of the molecules in the crystal lattice. Different polymorphs typically differ in their physical properties such as, for example, melting point, solubility, and chemical reactivity. Thus, the particular characteristics of the respective polymorphs can appreciably influence the solubility profile of a chemical substance. Further, the particular characteristics of the respective polymorphs can appreciably influence pharmaceutical properties such us dissolution rate and bioavailability.

Accordingly, there is a need to identify and isolate new polymorphic forms of sunitinib base, as well as to develop processes for producing sunitinib base in new polymorphic forms. In addition, there is a need for improved pharmaceutical compositions comprising sunitinib base in one or more polymorphic forms.

BRIEF SUMMARY OF THE INVENTION

The present invention provides crystalline polymorphic forms of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide, that is, sunitinib base, including polymorphic Form I, Form II, impure Form III, Form IV, and mixtures thereof.

The present invention also provides processes for preparing crystalline polymorphic fauns of sunitinib base, including polymorphic Form I, Form II, impure and known Form III, Form IV, and mixtures thereof.

The present invention further provides processes for preparing pharmaceutically acceptable salts of sunitinib base (e.g., sunitinib malate) using crystalline polymorphic forms of sunitinib base, including polymorphic Form I, Form II, known Form III, Form IV, and mixtures thereof.

The present invention also provides pharmaceutical compositions comprising N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide, that is, sunitinib base, including crystalline polymorphic Form I, Form II, Form III known and in impure forms, Form IV, mixtures thereof, and salts thereof, preferably compositions comprising a polymorphic form of sunitinib base selected from the group consisting of polymorphic Form I, polymorphic Form II, polymorphic Form IV, and mixtures of any one or more of polymorphic Form I, polymorphic Form II, polymorphic Form IV, and mixtures of at least one of polymorphic Form I, polymorphic Form II, polymorphic Form IV with impure Form III or known Form III.

DETAILED DESCRIPTION OF THE INVENTION

Applicants have discovered that sunitinib base can exist in several crystalline forms. These crystalline forms of sunitinib base have been prepared and characterized as described herein and are referred to herein as polymorphic Form I, Form II, Form III known and impure forms, and Form IV. The crystalline forms of sunitinib base can also be mixtures.

In accordance with some embodiments, the present invention provides crystalline polymorphic forms of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide, that is, sunitinib base, characterized using various analytical methods, including, for example, XRD, IR, and DSC.

In a particularly preferred embodiment, the present invention provides N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide polymorphic Form I.

Figure 1:
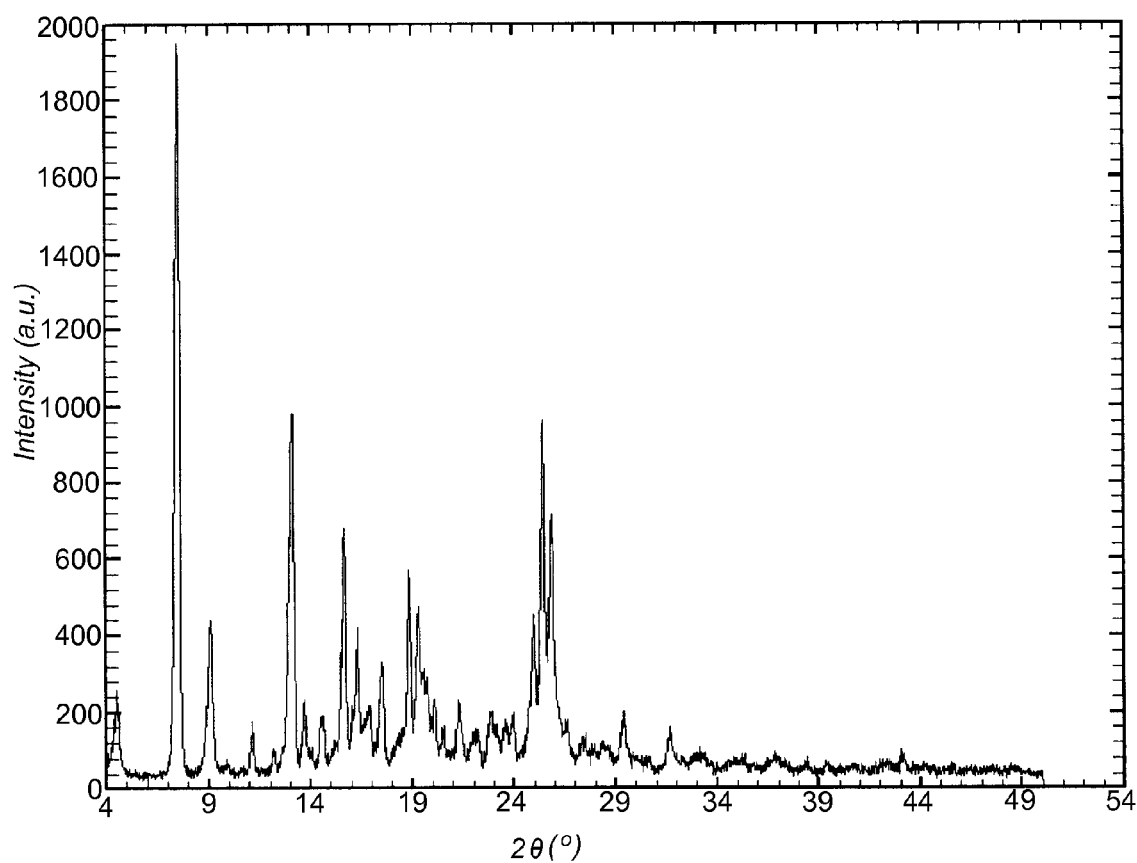
FIG. 1 is the X-ray powder diffractogram (XRD) of sunitinib base polymorphic Form I.

In some embodiments, the present invention provides sunitinib base polymorphic Form I having an XRD pattern substantially as shown in FIG. 1. Form I sunitinib base includes peaks at approximately 4.5, 7.5, 9.1, 11.1, 13.1, 15.6, 16.3, 17.5, 18.8, 19.3, 25.0, 25.4, 25.9, and 29.4 degrees 2θ (±0.2 degrees).

Figure 2:
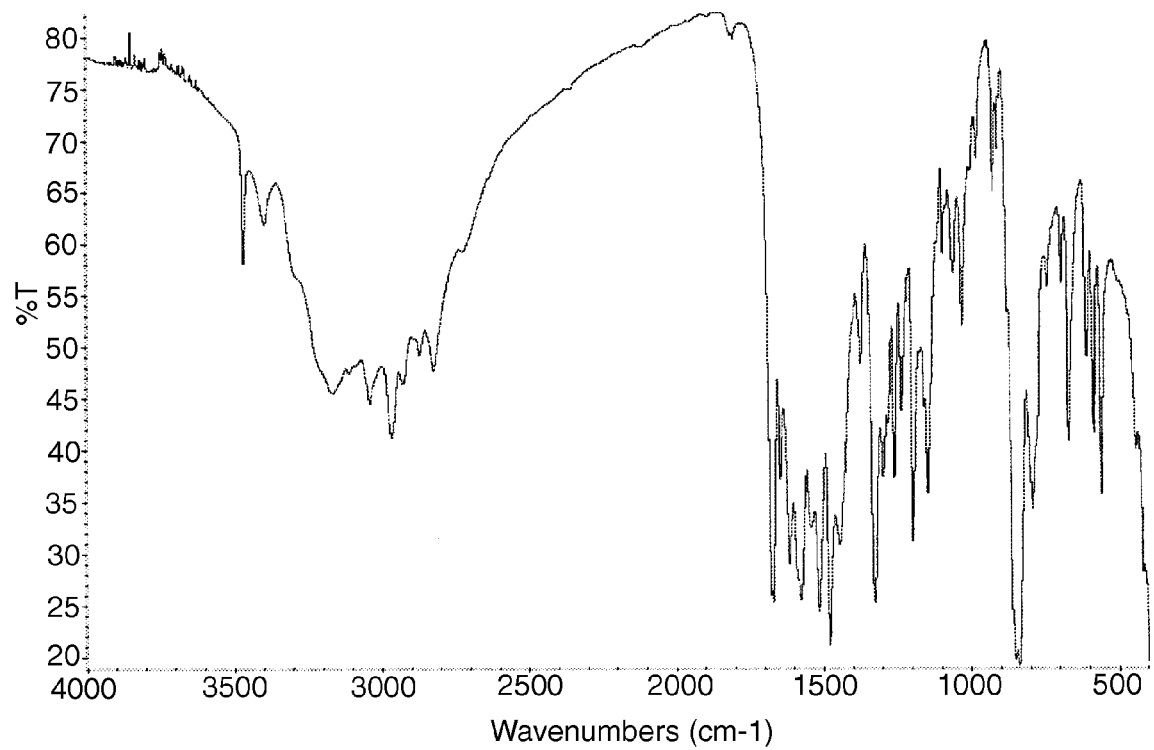
FIG. 2 is the Infrared (IR) spectrum of sunitinib base polymorphic Fat I.

In some embodiments, the present invention provides sunitinib base polymorphic Form I having an IR spectrum substantially as shown in FIG. 2. Form I sunitinib base includes peaks at approximately 3471, 3400, 3170, 3042, 2968, 2825, 1671, 1646, 1615, 1576, 1516, 1480, 1445, 1376, 1327, 1297, 1260, 1235, 1197, 1148, 1096, 1056, 1031, 983, 926, 912, 837, 791, 742, 695, 669, 609, 585, and 558 cm$^{-1}$.

Figure 3:
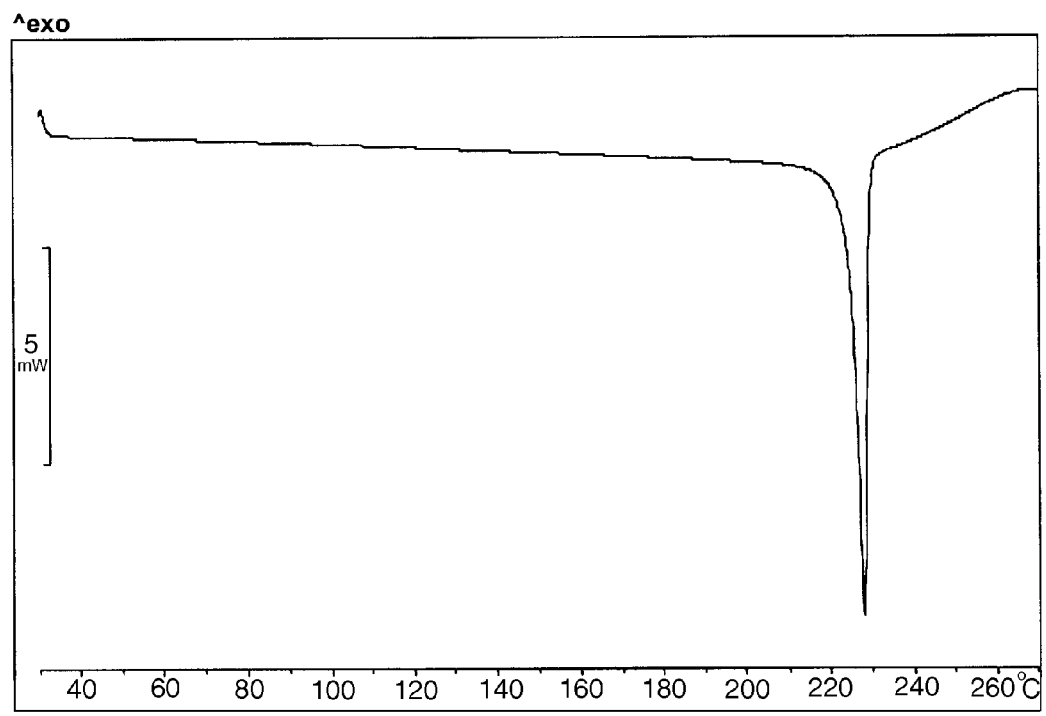
FIG. 3 is the Differential Scanning Calorimetry (DSC) thermogram in an open pan of sunitinib base polymorphic Form I.

In some embodiments, the present invention provides sunitinib base polymorphic Form I having a DSC thermogram in an open pan as substantially shown in FIG. 3. FIG. 3 illustrates the DSC thermogram in an open pan of sunitinib base polymorphic Form I which has an endothermic peak at approximately 227.2° C. with an onset of 224.5° C.

In another particularly preferred embodiment, the present invention provides N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide polymorphic Form II.

Figure 4:
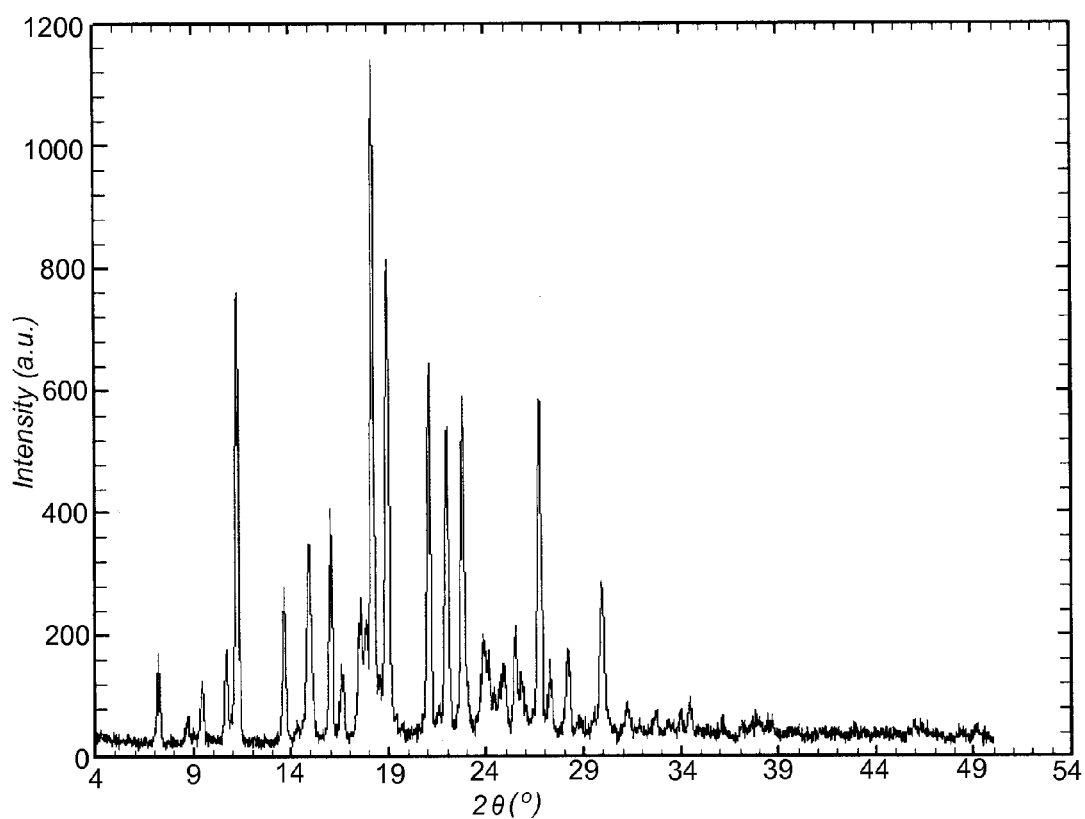
FIG. 4 is the XRD of sunitinib base polymorphic Form II.

In some embodiments, the present invention provides sunitinib base polymorphic Form II having an XRD pattern substantially as shown in FIG. 4. Form II sunitinib base includes peaks at approximately 7.2, 9.4, 10.7, 11.2, 13.6, 14.9, 16.0, 18.2, 18.9, 21.1, 22.0, 22.8, 26.7, and 29.9 degrees 2θ (±0.2 degrees).

Figure 5:
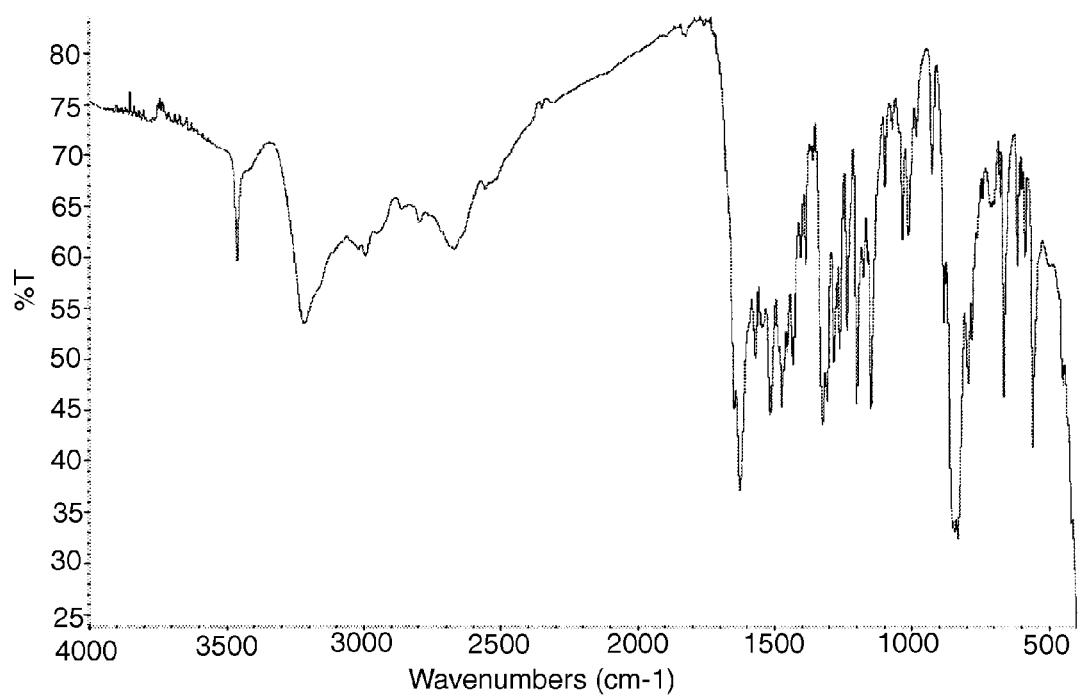
FIG. 5 is the IR spectrum of sunitinib base polymorphic Form II.

In some embodiments, the present invention provides sunitinib base polymorphic Form II having an IR spectrum as substantially shown in FIG. 5. Form II sunitinib base includes peaks at approximately 3464, 3219, 2672, 1626, 1570, 1516, 1473, 1432, 1404, 1386, 1325, 1308, 1282, 1264, 1235, 1200, 1175, 1149, 1097, 1069, 1034, 1012, 983, 925, 882, 832, 794, 780, 709, 677, 664, 615, 588, and 557 cm$^{-1}$.

Figure 6:
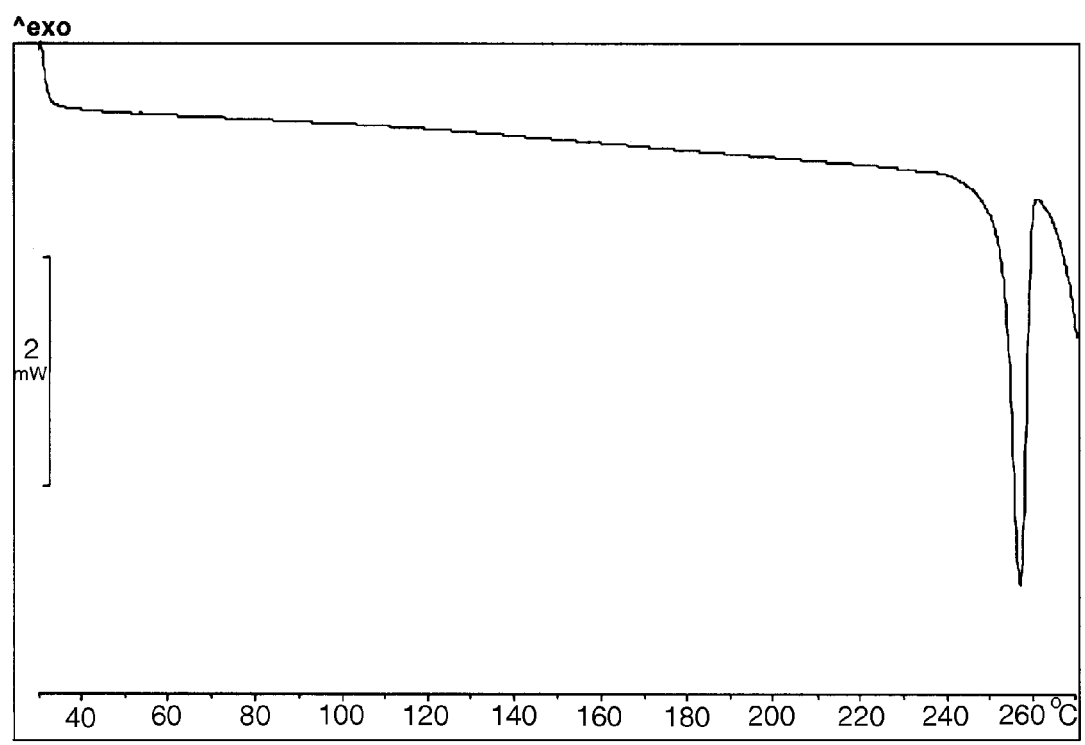
FIG. 6 is the Differential Scanning Calorimetry (DSC) thermogram in an open pan of sunitinib base polymorphic Form II.

In some embodiments, the present invention provides sunitinib base polymorphic Form II having a DSC thermogram in an open pan as substantially shown in FIG. 6. FIG. 6 illustrates the DSC thermogram in an open pan of sunitinib base polymorphic Form II which has an endothermic peak at approximately 256.6° C. with an onset of 252.7° C.

In another embodiment, the present invention provides characterization data for N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide polymorphic Form III both in impure and in pure forms.

Figure 7:
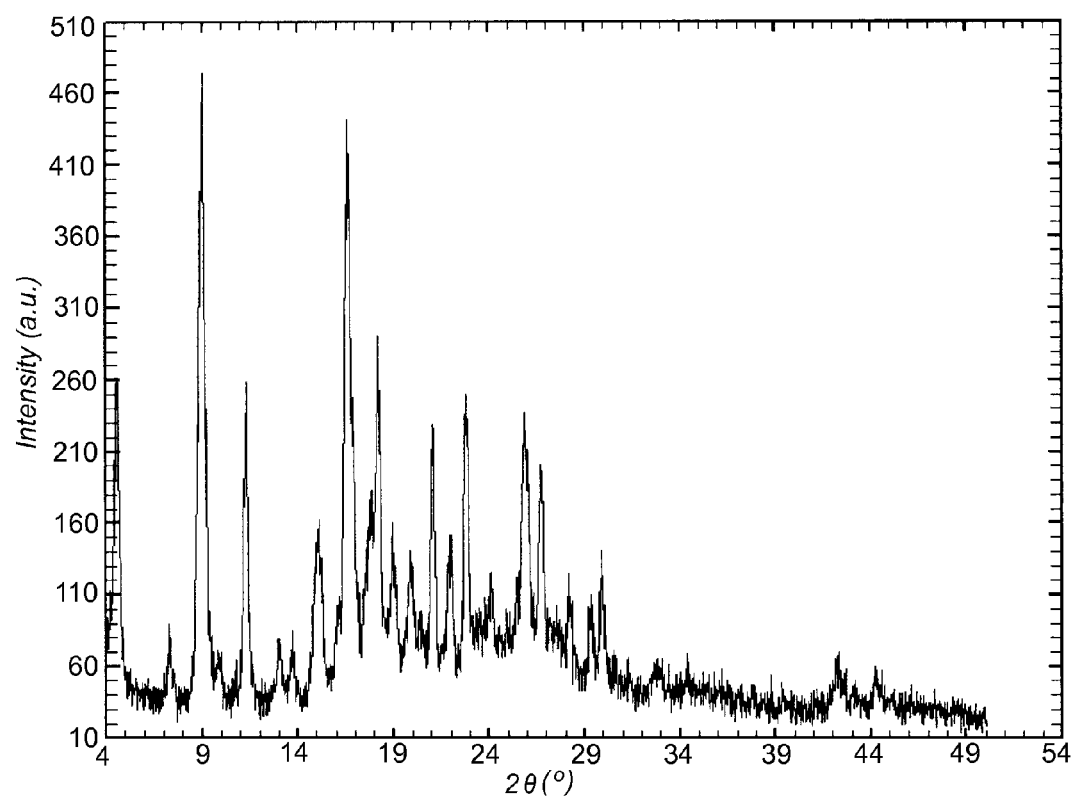
FIG. 7 is the XRD of sunitinib base impure polymorphic Form III.

In some embodiments, the present invention provides sunitinib base impure polymorphic Form III having an XRD pattern substantially as shown in FIG. 7. Impure Form III sunitinib base includes peaks at approximately 4.6, 9.0, 11.3, 13.0, 15.1, 16.6, 18.2, 19.0, 19.9, 21.1, 22.0, 22.8, 25.9, 26.7, and 29.9 degrees 2θ (±0.2 degrees).

Figure 8:
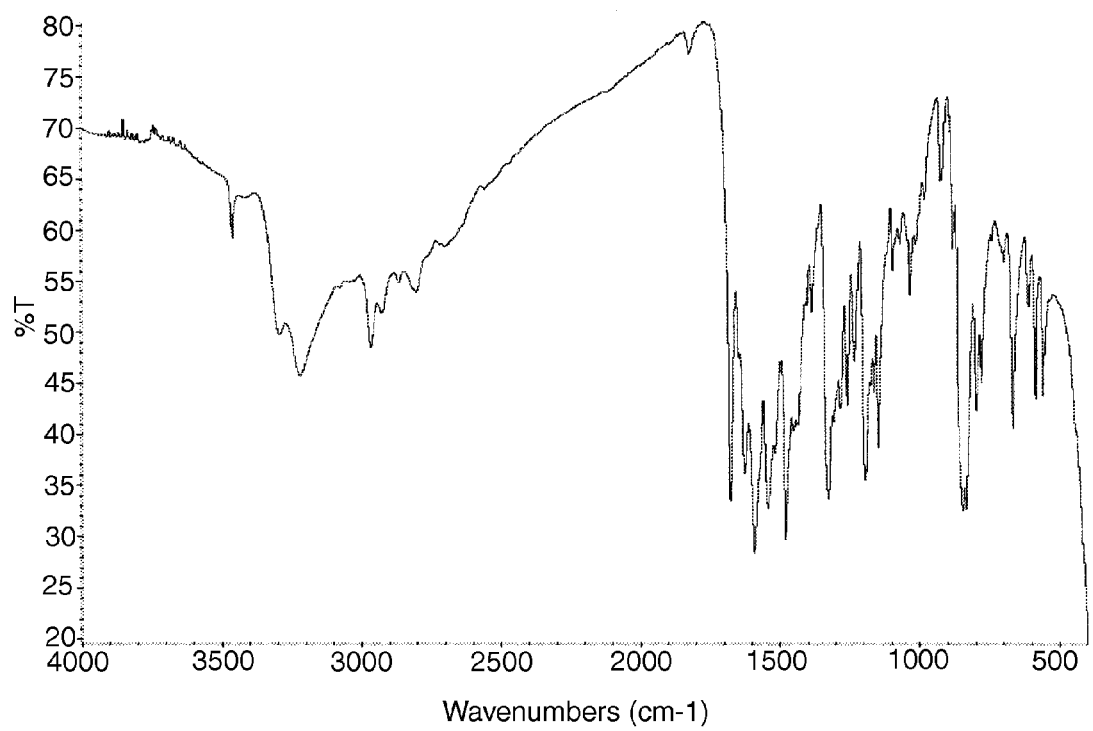
FIG. 8 is the IR spectrum of sunitinib base impure polymorphic Form III.

In some embodiments, the present invention provides sunitinib base impure polymorphic Form III having an IR spectrum as substantially shown in FIG. 8. Impure Form III sunitinib base includes peaks at approximately 3464, 3220, 2967, 1677, 1625, 1589, 1542, 1479, 1385, 1326, 1281, 1257, 1231, 1193, 1163, 1148, 1096, 1033, 924, 881, 844, 796, 779, 698, 665, 610, 585, and 557 cm$^{-1}$.

Figure 9:
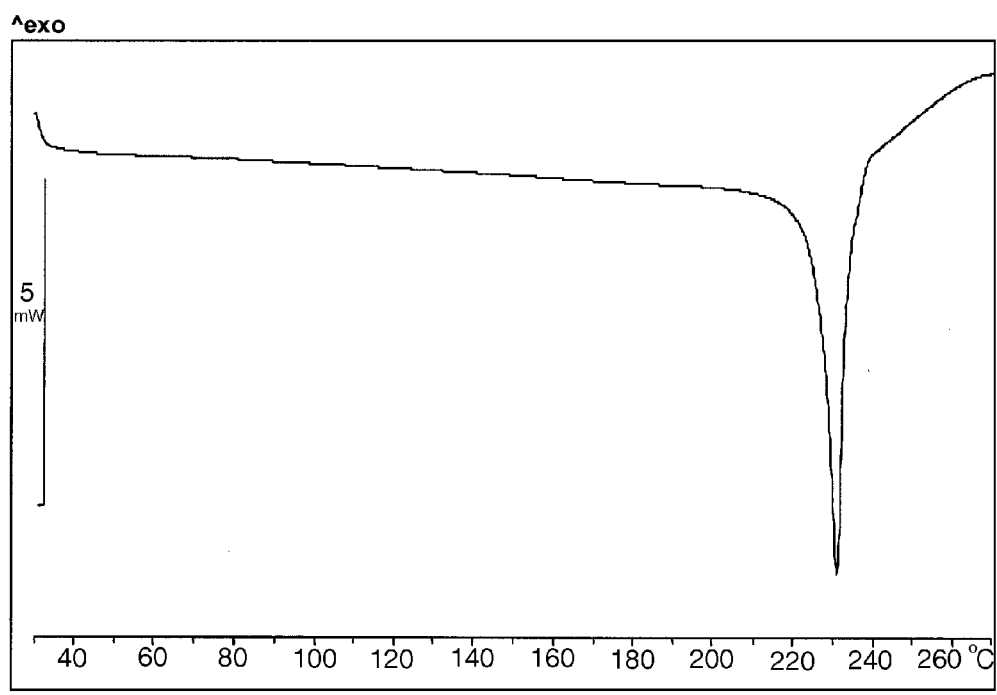
FIG. 9 is the DSC thermogram in an open pan of sunitinib base impure polymorphic Form III.

In some embodiments, the present invention provides sunitinib base impure polymorphic Form III having a DSC thermogram in an open pan as substantially shown in FIG. 9. FIG. 9 illustrates the DSC thermogram in an open pan of sunitinib base impure polymorphic Form III which has an endothermic peak at approximately 230.8° C. with an onset of 226.3° C.

Figure 13:
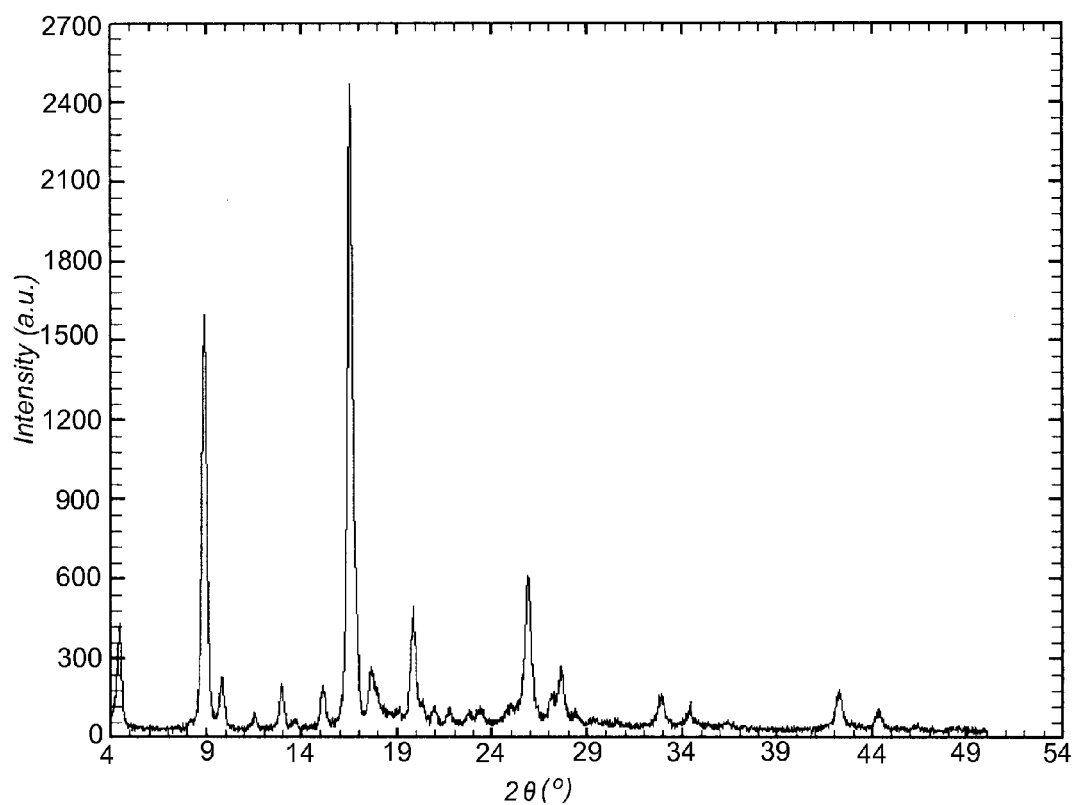
FIG. 13 is the XRD of sunitinib base polymorphic Form III.

In some embodiments, the present invention provides sunitinib base known polymorphic Form III having an XRD pattern substantially as shown in FIG. 13. Known Form III sunitinib base includes peaks at approximately 4.6, 8.9, 9.8, 12.9, 15.1, 16.5, 17.7, 19.8, 25.9, 27.6, 32.9, 34.4, 42.3, and 44.3 degrees 2θ (±0.2 degrees).

Figure 14:
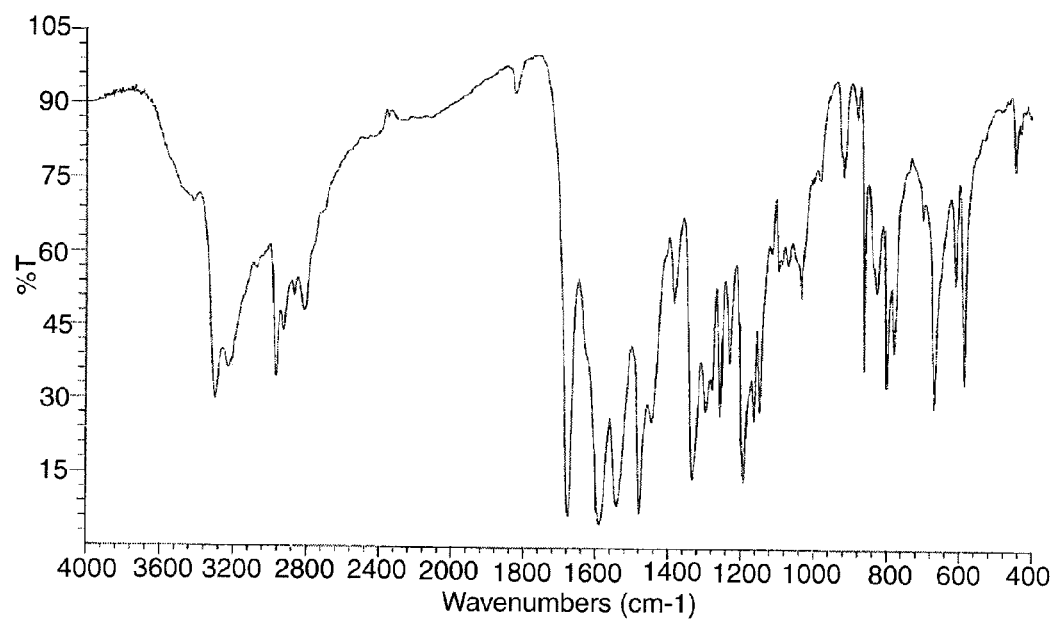
FIG. 14 is the IR spectrum of sunitinib base polymorphic Form III.

In some embodiments, the present invention provides sunitinib base known polymorphic Form III having an IR spectrum as substantially shown in FIG. 14. Known Form III sunitinib base includes peaks at approximately 3418, 3298, 3227, 2966, 2926, 2868, 2814, 1823, 1676, 1589, 1541, 1479, 1447, 1383, 1333, 1296, 1277, 1256, 1229, 1192, 1163, 1148, 1113, 1095, 1086, 1068, 1034, 1001, 982, 924, 916, 879, 860, 825, 798, 779, 698, 669, 609, 584, and 444 cm$^{-1}$.

Figure 15:
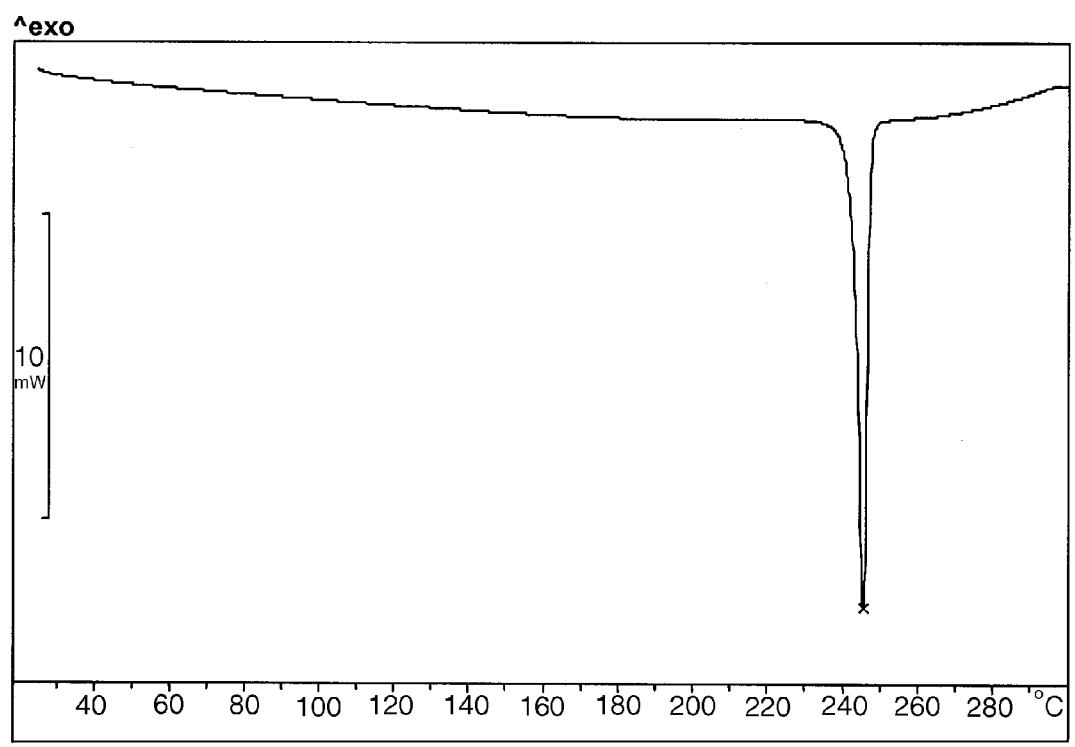
FIG. 15 is the DSC thermogram in an open pan of sunitinib base polymorphic Form III.

In some embodiments, the present invention provides sunitinib base known polymorphic Form III having a DSC thermogram in an open pan as substantially shown in FIG. 15. FIG. 15 illustrates the DSC thermogram in an open pan of sunitinib base known polymorphic Form III which has an endothermic peak at approximately 244.5° C. with an onset of 242.2° C.

In yet another particularly preferred embodiment, the present invention provides N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide polymorphic Form IV.

Figure 10:
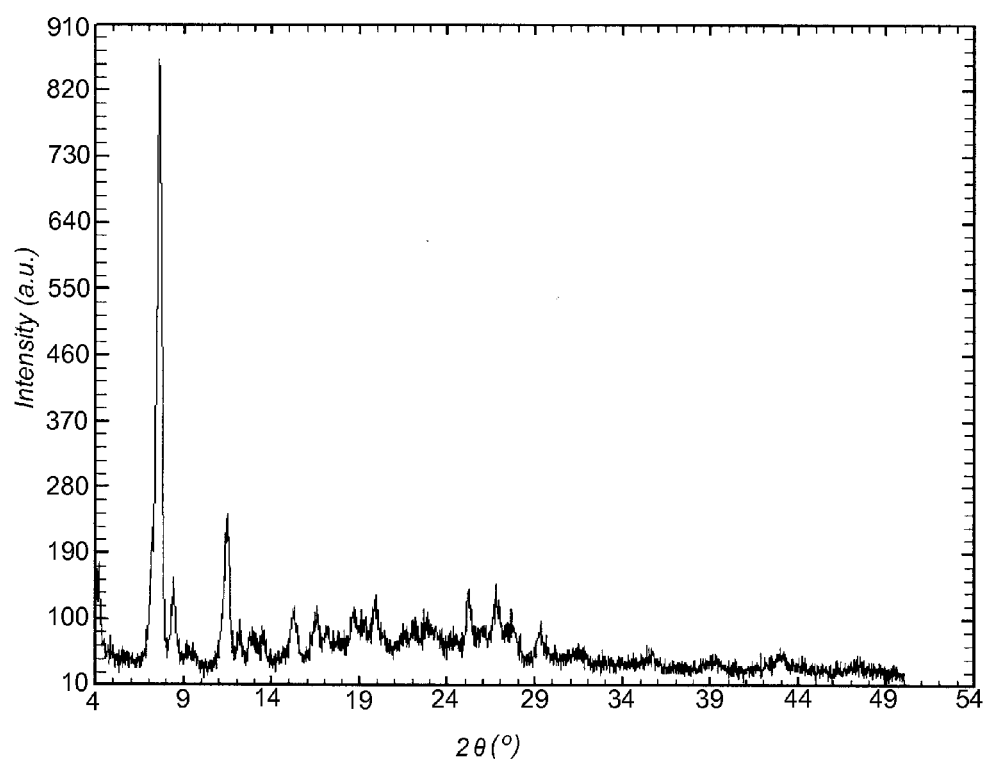
FIG. 10 is the XRD of sunitinib base polymorphic Form IV.

In some embodiments, the present invention provides sunitinib base polymorphic Form IV having an XRD pattern substantially as shown in FIG. 10. Form IV sunitinib base includes peaks at approximately 4.2, 7.6, 8.4, 11.4, and 25.2 degrees 2θ (±0.2 degrees).

Figure 11:
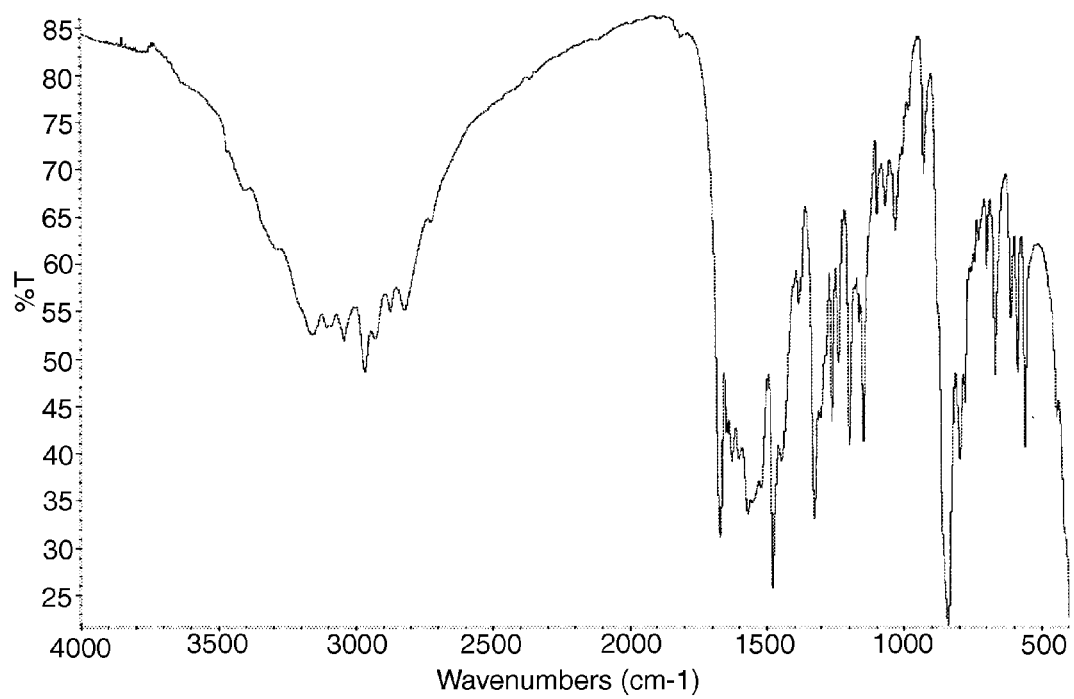
FIG. 11 is the IR spectrum of sunitinib base polymorphic Form IV.

In some embodiments, the present invention provides sunitinib base polymorphic Form IV having an IR spectrum as substantially shown in FIG. 11. Form IV sunitinib base includes peaks at approximately 3043, 2968, 2823, 1672, 1626, 1569, 1478, 1383, 1327, 1261, 1238, 1199, 1147, 1095, 1067, 1030, 926, 840, 795, 778, 697, 667, 609, 585, and 557 cm$^{-1}$.

Figure 12:
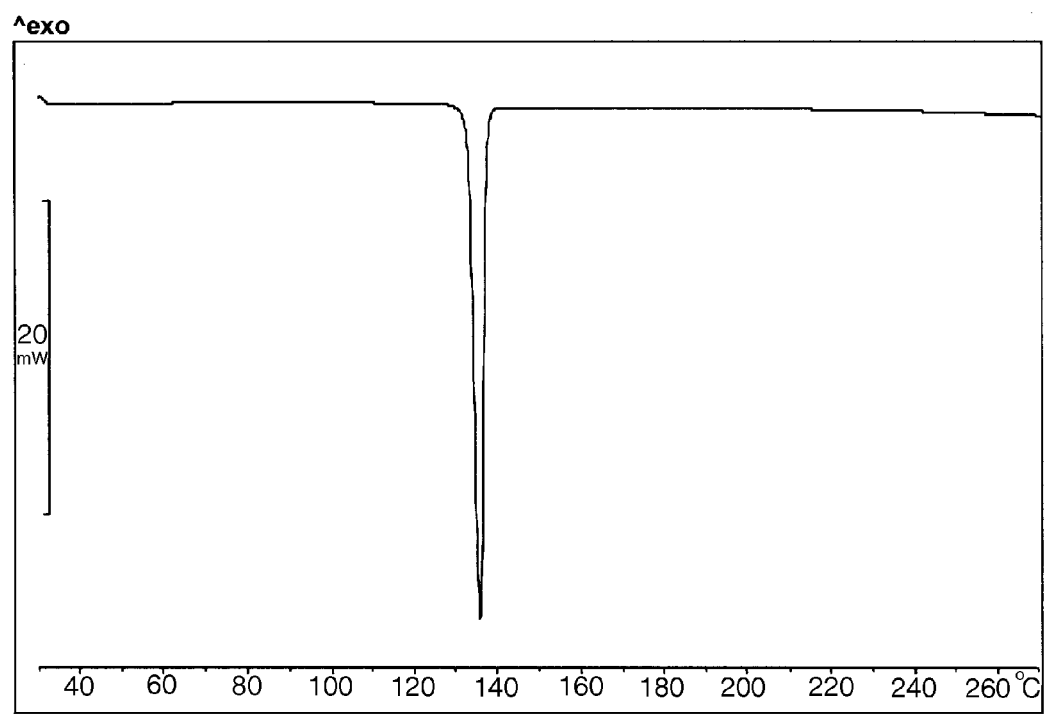
FIG. 12 is the DSC thermogram in an open pan of sunitinib base polymorphic Form IV.

In some embodiments, the present invention provides sunitinib base polymorphic Form IV having a DSC thermogram in an open pan substantially shown in FIG. 12. FIG. 12 illustrates the DSC thermogram in an open pan of sunitinib base polymorphic Form IV which has an endothermic peak at approximately 134.1° C. with an onset of 132.8° C.

In keeping with other aspects of the invention, the present invention provides processes for preparing crystalline polymorphic forms of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (i.e., sunitinib base). In accordance with the invention, processes for preparing crystalline polymorphic forms of sunitinib base typically comprise forming a suspension or a solution of sunitinib base in a solvent, and separating or isolating the polymorphic form of sunitinib base from the solvent.

The sunitinib base used for preparing polymorphic forms of sunitinib base of the present invention can be from any suitable source. For example, the sunitinib base starting material can be obtained by any known method. Alternatively, the sunitinib base starting material can be other polymorphic forms of sunitinib base (e.g., Form I, Form II, known Form III, impure Form III, Form IV, and mixtures thereof).

Illustrative solvents useful in processes of the invention include, for example, dichloromethane, methyl tert-butyl ether, n-butyl acetate, i-propyl acetate, water, toluene, heptane, dimethylformamide, methanol, ethanol, tetrahydrofuran, 2-propanol, n-butanol, 2-butanone, acetonitrile, chloroform, and mixtures thereof.

The present invention provides a process for preparing sunitinib base polymorphic Form I, said process comprising (i) suspending sunitinib base in a solvent to form a suspension and (ii) removing the solvent from said suspension, to give sunitinib base polymorphic Form I. Preferably, step (i) is conducted at a temperature of from about 25° C. to about 70° C. In other preferred embodiments, step (ii) is conducted by filtering the suspension. In particularly preferred embodiments, the solvent comprises dichloromethane, n-butyl acetate, i-propyl acetate, water, toluene, heptane, or a 20:80 mixture of water and ethanol.

The present invention provides a process for preparing sunitinib base polymorphic Form II, said process comprising (i) dissolving sunitinib base in a solvent which comprises methanol to form a solution, and (ii) removing the solvent from said solution, to give sunitinib base polymorphic Form II. Preferably, the solvent is methanol. In other preferred embodiments, step (i) is conducted at reflux. It is also preferred that step (ii) is conducted by stirring the solution at room temperature to obtain a suspension and filtering the suspension.

The present invention provides a process for preparing sunitinib base impure polymorphic Foam III, said process comprising (i) suspending sunitinib base in a solvent to form a suspension and (ii) removing the solvent from said suspension, to give sunitinib base impure polymorphic Form III. Preferably, step (i) is conducted at a temperature of from about 50° C. to about 70° C. In other preferred embodiments, step (ii) is conducted by evaporating the solvent. In particularly preferred embodiments, the solvent comprises tetrahydrofuran, ethanol, 2-propanol, n-butanol, 2-butanone, or acetonitrile.

The present invention provides a process for preparing sunitinib base known polymorphic Form III, said process comprising (i) precipitating sunitinib base known polymorphic Form III from a solvent to form a suspension and (ii) removing the solvent from said suspension, to give sunitinib base polymorphic Form III. Preferably, step (i) is carried out directly from the reaction crude. In particularly preferred embodiments, the solvent comprises ethanol, 2-propanol, or n-butanol.

The present invention provides a process for preparing sunitinib base known polymorphic Form III, said process comprising (i) suspending sunitinib base in a solvent to form a suspension and (ii) removing the solvent from said suspension, to give sunitinib base polymorphic Form III. Preferably, step (i) is conducted at a temperature not higher than about 95° C. In particularly preferred embodiments, the solvent comprises acetonitrile, ethanol, 2-propanol, or n-butanol.

The present invention provides a process for preparing sunitinib base known polymorphic Form III, said process comprising (i) dissolving sunitinib base in n-butanol to form a solution, and (ii) removing the solvent from said solution, to give sunitinib base polymorphic Form III. Preferably, step (i) is conducted at a temperature higher than about 110° C. In other preferred embodiments, step (ii) is conducted by stirring the solution at about 0-5° C. to obtain a suspension and filtering the suspension.

The present invention provides a process for preparing sunitinib base polymorphic Form IV, said process comprising (i) suspending sunitinib base in chloroform to form a suspension and (ii) removing the chloroform from said suspension, to give sunitinib base polymorphic Form IV. Preferably, step (i) is conducted at a temperature of about 50° C. In other preferred embodiments, step (ii) is conducted by evaporating the chloroform.

In keeping with other aspects, the present invention provides a process for preparing pharmaceutically acceptable salts of sunitinib (e.g., sunitinib malate) comprising reacting sunitinib base with a salt forming reagent, wherein the sunitinib base is selected from the group consisting of sunitinib base polymorphic Form I, Form II, or Form IV. It is also possible to form the salt form of mixtures of sunitinib base polymorphic Form I, Form II, known Form III and Form IV in all the various combinations, such as the salt form of sunitinib base polymorphic Forms I and II, Forms I and known III, Forms II and known III, and the like, as well as all four of Forms I-IV. In preferred embodiments, the salt forming reagent is a malate salt forming reagent.

In keeping with other aspects, the present invention also provides pharmaceutical compositions comprising sunitinib base and salts of sunitinib base polymorphic Form I, Form II, Form III, Form IV, and mixtures thereof. In some preferred embodiments, the present invention provides compositions comprising a polymorphic foam of sunitinib base selected from the group consisting of polymorphic Form I, polymorphic Form II, polymorphic Form IV, and mixtures of any two or more of polymorphic Form I, polymorphic Form II, polymorphic Form IV. In other embodiments, the present invention provides compositions comprising mixtures of at least one of polymorphic Form I, polymorphic Form II, polymorphic Form IV with impure Form III or known Form III.

Similarly, pharmaceutical compositions can comprise mixtures of any of the polymorphic forms of sunitinib base and salts of polymorphic forms of sunitinib base in all various combinations and permutations. In other preferred embodiments, the salts of sunitinib base is the malate salt.

The following examples further illustrate the invention but, of course, should not be construed as in any way limiting its scope.

EXAMPLES

The XRD diffractograms were obtained using a RX SIEMENS D5000 diffractometer with a vertical goniometer, a copper anodic tube, and radiation $CuK_\alpha$, $\lambda=1.54056$ Å.

Fourier transform IR spectra were acquired either on a Thermo Nicolet Nexus spectrometer or on a Shimadzu FT-IR 8400S spectrophotometer, and polymorphs were characterized in potassium bromide pellets.

DSC measurements were performed in vented pan at a scan rate of 10° C./minute from 25.0° C. to 290.0° C. under a nitrogen purge with a DSC823 available from Mettler-Toledo.

Comparative Example 1

This example was carried out following the teachings of Example 80 (Alternative Synthesis) of U.S. Pat. No. 6,573,293.

N-[2-(diethylamino)ethyl]-5-formyl-2,4-dimethyl-1H-pyrrole-3-carboxamide (5.00 g), 5-fluoro-2-oxindole (2.85 g) and ethanol (80 mL) were stirred at room temperature. Pyrrolidine (80 µL) was then added and the suspension was heated to reflux. Complete dissolution of the materials was observed at 47° C. and after 30 minutes at reflux an orange solid started to crystallize. The reaction was monitored by TLC and was shown to be complete after 3 h at reflux. The mixture was cooled to room temperature and stirred for 30 minutes. The mixture was filtered, and the collected solid was washed with 25 mL of ethanol. The solid was dried at 54° C. for 4 h under vacuum to give 6.65 g (88.6% yield) of light orange solid.

Analytical data: XRD: Form III, substantially identical to FIG. 13.

4.50 g of the solid was stirred in 40 mL of ethanol and heated to reflux. The suspension was stirred for 30 minutes, cooled to room temperature, and stirred for an additional 30 minutes. The thick suspension was filtered, and the collected solid was washed with ethanol (15 mL) and dried at 54° C. for 4 hours under vacuum to give 4.24 g (94.2% yield) of light orange solid.

Analytical data: XRD: Analytical data: XRD: Form III, See FIG. 13. IR: Form III, See FIG. 14; DSC (open pan): Form III, See FIG. 15.

These results demonstrate that sunitinib base polymorphic Form III is the polymorphic form obtained in the prior art.

Example 1

This example illustrates a process for preparing sunitinib base polymorphic Form I in accordance with an embodiment of the invention.

Sunitinib base (500 mg) was suspended in water (2.5 mL), adjusted to pH 11 and stirred for 1 hour. The mixture was filtered and resuspended in water (2.5 mL) for 1 hour. The mixture was filtered and dried under vacuum at 40° C.

Analytical data: XRD: Form I, substantially identical to FIG. 1.

These results demonstrate that a process in accordance with the invention can produce sunitinib base polymorphic Form I.

Examples 2-8

These examples illustrate a process for preparing sunitinib base polymorphic Form I in accordance with embodiments of the invention.

The following general procedure was followed: sunitinib base (100 mg) was suspended in a solvent (1 mL) and heated (in a closed vial) at the temperature indicated in Table 1 for 1 hour. The mixtures were allowed to cool to ambient temperature, stirred for 24 hours at this temperature before evaporation of the solvent (by opening the vial and allowing to evaporate under ambient temperature pressure conditions). The results are summarized in Table 1.

TABLE 1

| Example | Solvent | T (° C.) | XRD Result |
|---|---|---|---|
| 2 | dichloromethane | 25 | Form I |
| 3 | n-butyl acetate | 70 | Form I |
| 4 | i-propyl acetate | 70 | Form I |
| 5 | water | 70 | Form I |
| 6 | toluene | 70 | Form I |
| 7 | heptane | 70 | Form I |
| 8 | water/ethanol(20:80) | 70 | Form I |

Analytical data of Examples 2-6 and 8: XRD: Form I, substantially identical to FIG. 1.

Analytical data of Example 7: XRD: Form I, see FIG. 1; IR: Form I, see FIG. 2; DSC (open pan): Form I, see FIG. 3.

These results demonstrate processes for preparing sunitinib base polymorphic Form I in accordance with embodiments of the invention.

Example 9

This example illustrates a process for preparing sunitinib base polymorphic Form II in accordance with an embodiment of the invention.

Sunitinib base (300 mg) was dissolved in methanol (25 mL) at reflux and allowed to cool to ambient temperature. The mixture was filtered and dried under vacuum at 40° C.

Analytical data: XRD: Form II, see FIG. 4; IR: Form II, see FIG. 5; DSC (open pan): Form II, see FIG. 6.

These results demonstrate that a process in accordance with the invention can produce sunitinib base polymorphic Form II.

Examples 10-16

These examples illustrate processes for preparing sunitinib base polymorphic Form III in accordance with embodiments of the invention.

The following general procedure was followed: sunitinib base (100 mg) was suspended in a solvent (1 mL) and heated (in a closed vial) at the temperature indicated in Table 2 for 1 hour. The mixtures were allowed to cool to ambient temperature, stirred for 24 hours at this temperature before evaporation of the solvent (by opening the vial and allowing to evaporate under ambient temperature pressure conditions). The results are summarized in Table 2.

TABLE 2

| Example | Solvent | T (° C.) | XRD Result |
| --- | --- | --- | --- |
| 10 | THF | 50 | Impure Form III |
| 11 | Ethanol | 70 | Impure Form III |
| 12 | 2-butanone | 70 | Impure Form III |
| 13 | 2-propanol | 70 | Impure Form III |
| 14 | n-butanol | 70 | Impure Form III |
| 15 | Acetonitrile | 70 | Impure Form III |
| 16 | Acetonitrile | 70 | Form III |

Analytical data of Examples 10-14: XRD: Impure Form III, substantially identical to FIG. 7.

Analytical data of Example 15: XRD: Impure Form III, see FIG. 7; IR: Impure Form III, see FIG. 8; DSC (open pan): Impure Form III, see FIG. 9.

Analytical data of Example 16: XRD: Form III, substantially identical to FIG. 13; IR: Form III, substantially identical to FIG. 14; DSC (open pan): Form III, substantially identical to FIG. 15.

These results demonstrate processes for preparing sunitinib base polymorphic Form III in accordance with embodiments of the invention.

Examples 17-21

These examples illustrate processes for preparing mixtures of sunitinib base comprising polymorphic Form I and Form III, or comprising polymorphic Form I, II, and III in accordance with embodiments of the invention.

The following general procedure was followed: sunitinib base (100 mg) was suspended in solvent (1 mL) and heated (in a closed vial) at the temperature indicated in Table 3 for 1 hour. The mixtures were allowed to cool to ambient temperature, stirred for 24 hours at this temperature before evaporation of the solvent (by opening the vial and allowing to evaporate under ambient temperature pressure conditions, except entry 21 that was dried under vacuum). The results are summarized in Table 3.

TABLE 3

| Example | Solvent | T (° C.) | XRD Result |
| --- | --- | --- | --- |
| 17 | methanol | 50 | mixture of Form I, Form II and Form III |
| 18 | methyl isobutylketone | 70 | mixture of Form I, Form II and Form III |
| 19 | ethyl acetate | 70 | mixture of Form I, Form II and Form III |
| 20 | MTBE | 50 | mixture of Form I, Form II and Form III |
| 21 | dimethylformamide | 70 | mixture of Form I and Form III |

These results demonstrate processes for preparing mixtures of sunitinib base comprising polymorphic Form I and Form III, or comprising polymorphic Form I, II, and III in accordance with embodiments of the invention.

Example 22

This example illustrates a process for preparing sunitinib base polymorphic Form IV in accordance with an embodiment of the invention.

Sunitinib base (100 mg) was suspended in chloroform (1 mL) and heated (in a closed vial) at 50° C. for 1 hour. The mixture was allowed to cool to ambient temperature, stirred for 24 hours at this temperature before evaporation of the solvent (by opening the vial and allowing to evaporate under ambient temperature pressure conditions).

Analytical data: XRD: Form IV, see FIG. 10; IR: Form IV, see FIG. 11; DSC (open pan): Form IV, see FIG. 12.

These results demonstrate that a process in accordance with the invention can produce sunitinib base polymorphic Form IV.

Example 23

This example illustrates a process for preparing sunitinib base polymorphic Form III in accordance with an embodiment of the invention.

N-[2-(diethylamino)ethyl]-5-formyl-2,4-dimethyl-1H-pyrrole-3-carboxamide (10.03 g), 5-fluoro-2-oxindole (5.70 g) and 2-propanol (100 mL) were stirred at room temperature. Pyrrolidine (160 µL) was then added and the suspension was heated to reflux. Complete dissolution of the materials was observed at 44° C. and after 20 minutes at reflux an orange solid started to crystallize. The suspension became very thick quickly. The reaction was monitored by TLC and after 3 h at reflux it was complete. The mixture was cooled down to room temperature and stirred for 30 minutes. The thick light orange suspension was then filtered and the collected solid was washed with 33 mL of 2-propanol to give 15.90 g of light orange solid (LOD=13.51%, yield=91.2%).

Analytical data: XRD: Form III, substantially identical to FIG. 13.

14.62 g of solid were stirred in 102 mL of 2-propanol and heated to 72° C. The suspension was stirred for 30 minutes, cooled to room temperature and stirred for further 30 minutes. The thick suspension was filtered, the collected solid was washed with 20 mL of 2-propanol and the solid was dried at 54° C. for 4 hours under vacuum to give 12.36 g (97.8% yield) of light orange solid.

Analytical data: XRD: Form III, substantially identical to FIG. 13; IR: Form III, substantially identical to FIG. 14; DSC (open pan): Form III, substantially identical to FIG. 15.

Example 24

This example illustrates a process for preparing sunitinib base polymorphic Form III in accordance with an embodiment of the invention.

Sunitinib base obtained in Example 23 (1.23 g) was stirred in 25 mL of n-butanol and heated to dissolution. At 111° C. a red clear solution was obtained. The mixture was then cooled down to 0-5° C., stirred for 30 minutes and filtered. The collected solid was washed with 2×10 mL of n-butanol and the solid was dried at 60° C. for 4 hours under vacuum to give 1.01 g (82.1% yield) of light orange solid.

Analytical data: XRD: Form III, substantially identical to FIG. 13; IR: Form III, substantially identical to FIG. 14; DSC (open pan): Form III, substantially identical to FIG. 15.

Example 25

This example illustrates a process for preparing sunitinib base polymorphic Form III in accordance with an embodiment of the invention.

N-[2-(diethylamino)ethyl]-5-formyl-2,4-dimethyl-1H-pyrrole-3-carboxamide (10.02 g), 5-fluoro-2-oxindole (5.70 g) and n-butanol (100 mL) were stirred at room temperature.

Pyrrolidine (160 μL) was then added and the suspension was heated to 94° C. Complete dissolution of the materials was observed at 47° C., and once at 94° C. an orange solid started to crystallize. After 30 minutes at 94° C. the suspension was very thick. The reaction was monitored by TLC and after 2 h at 94° C. it was complete. The mixture was cooled to room temperature and stirred for 30 minutes. The thick light orange suspension was then filtered and the collected solid was washed with 40 mL of n-butanol to give 26.77 g of light orange solid (LOD=44.31%, yield=89.1%).

Analytical data: XRD: Form III, substantially identical to FIG. 13.

21.94 g of wet solid were stirred in 88 mL of n-butanol and heated to 95° C. The suspension was stirred for 30 minutes, cooled to room temperature and stirred for further 30 minutes. The thick suspension was filtered, the collected solid was washed with 37 mL of n-butanol and the solid was dried at 60° C. for 4 hours under vacuum to give 11.05 g (101.0% yield) of light orange solid.

Analytical data: XRD: Form III, substantially identical to FIG. 13; IR: Form III, substantially identical to FIG. 14; DSC (open pan): Form III, substantially identical to FIG. 15.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing a pharmaceutically acceptable salt of sunitinib comprising reacting sunitinib base with a salt forming reagent, wherein the sunitinib base is a polymorphic form selected from the group consisting of sunitinib base polymorphic Form I having an X-ray diffraction pattern (2θ) having characteristic peaks at 4.5, 7.5, 9.1, 11.1, 13.1, 15.6, 16.3, 17.5, 18.8, 19.3, 25.0, 25.4, 25.9 and 29.4 degrees 2θ (±0.2 degrees) and sunitinib base polymorphic Form II having an X-ray diffraction pattern (2θ) having characteristic peaks at 7.2, 9.4, 10.7, 11.2, 13.6, 14.9, 16.0, 18.2, 18.9, 21.1, 22.0, 22.8, 26.7, and 29.9 degrees 2θ (±0.2 degrees).

2. The process of claim 1, wherein the salt forming reagent is a malate salt forming reagent and the pharmaceutically acceptable salt of sunitinib is sunitinib malate.

3. The process of claim 1, wherein the salt forming reagent is malic acid and the pharmaceutically acceptable salt of sunitinib is sunitinib malate.

* * * * *